United States Patent
Yabusaki

(10) Patent No.: US 8,236,180 B2
(45) Date of Patent: Aug. 7, 2012

(54) BORON REMOVAL METHOD UTILIZING SUGAR AMIDE DERIVATIVE

(75) Inventor: Katsumi Yabusaki, Tsukuba (JP)

(73) Assignee: Kowa Company, Ltd., Nagoya-shi, Aichi (JP)

( * ) Notice: Subject to any disclaimer, the term of this patent is extended or adjusted under 35 U.S.C. 154(b) by 303 days.

(21) Appl. No.: 12/600,215

(22) PCT Filed: May 21, 2008

(86) PCT No.: PCT/JP2008/059305
§ 371 (c)(1),
(2), (4) Date: Nov. 13, 2009

(87) PCT Pub. No.: WO2008/146666
PCT Pub. Date: Dec. 4, 2008

(65) Prior Publication Data
US 2010/0294722 A1    Nov. 25, 2010

(30) Foreign Application Priority Data
May 23, 2007   (JP) .................... 2007-136436

(51) Int. Cl.
*C02F 1/28* (2006.01)
(52) U.S. Cl. ........ 210/666; 210/667; 210/683; 210/725; 210/735; 210/902
(58) Field of Classification Search .......... 210/665–667, 210/683, 724, 725, 727, 728, 735, 902
See application file for complete search history.

(56) References Cited

U.S. PATENT DOCUMENTS

| | | |
|---|---|---|
| 5,352,386 A | 10/1994 | Rahman et al. |
| 5,641,480 A | 6/1997 | Vermeer |
| 5,653,970 A | 8/1997 | Vermeer |

(Continued)

FOREIGN PATENT DOCUMENTS

DE    2 321 752    11/1974

(Continued)

OTHER PUBLICATIONS

International Search Report issued to the international application dated Aug. 26, 2008.

(Continued)

*Primary Examiner* — Matthew Savage
(74) *Attorney, Agent, or Firm* — Knobbe, Martens, Olson & Bear, LLP

(57) ABSTRACT

Disclosed is a boron adsorbent having an excellent adsorbing ability against boron contained in a solution, which is inexpensive and has high general versatility. Also disclosed is a boron removal method which can remove boron efficiently in a simple manner. An amide derivative represented by the general formula (1) is added to a boron-containing water under alkaline conditions to cause the adsorption of boron to the amide derivative. Then, a cation source having two or more valencies is added to the water to cause the aggregation of the amide body. The aggregated amide body is removed from the water. In the general formula (1), m represents 1 or 2; X represents —$CH_2OH$, —CHO or —COOH; n represents an integer of 2 to 5; X are independent from each other and n are independent from each other when m represents 2; and Y represents a monovalent hydrocarbon group having 6 to 16 carbon atoms when m is 1, and represents a divalent hydrocarbon group having 8 to 18 carbon atoms when m is 2.

6 Claims, 7 Drawing Sheets

U.S. PATENT DOCUMENTS 7,846,339 B2 * 12/2010 Suzuki et al. .............. 210/728

FOREIGN PATENT DOCUMENTS

| FR | 2 523 962 | 9/1983 |
|---|---|---|
| JP | 61-153193 | 7/1986 |
| JP | 01-229009 | 9/1989 |
| JP | 05-139999 | 6/1993 |
| JP | 2002-030052 | 1/2002 |
| JP | 2002-173664 | 6/2002 |
| JP | 2003-064128 | 3/2003 |
| JP | 2004-298738 | 10/2004 |
| WO | WO 95/15330 | 6/1995 |

OTHER PUBLICATIONS

Baeyens-Volant, et al. "A New Family of Liquid Crystals: N-substituted Aldonamides II: Relationship Between Chemical Structure and the Formation of Mesophases," *Molecular Crystals and Liquid Crystals*, vol. 135, pp. 93-110, 1986.

Syper, et al. Synthesis and Surface Properties of N-Alkylaldonamides, *Progress in Colloid & Polymer Science*, vol. 110, pp. 199-203, 1998.

Baeyens-Volant, et al, "A New Family of Liquid Crystals: N-substituted Aldonamides II: Relationship Between Chemical Structure and the Formation of Mesophases," *Molecular Crystals and Liquid Crystals*, vol. 135, pp. 93-110, 1986.

Briggs, et al. "Synthesis and Properties of Some Novel Nonionic Polyol Surfactants," *Journal of the Chemical Society*, pp. 379-380, 1995.

Fieser, et al. "Synthetic Emulsifying Agents," *Journal of the American Chemical Society*, vol. 78, pp. 2825-2832, 1956.

Frankel, et al. "Supramolecular Assemblies of Diacetylenic Aldonamides," *Journal of the American Chemical Society*, vol. 116, pp. 10057-10069, 1994.

Pilakowska-Pietras, et al. "Investigations on Foamability of Surface-chemically Pure Aqueous Solutions of Functionalized Alkylaldonamides," *Journal of Colloid and Interface Science*, vol. 294, pp. 423-428, 2006.

Syper, et al. Synthesis and Surface Properties of N-Alkylaldonamides,' *Progress in Colloid & Polymer Science*, vol. 110, pp. 199-203, 1998.

Supplementary European Search Report dated Apr. 13, 2011, issued to corresponding European patent application No. 08764428.2.

* cited by examiner

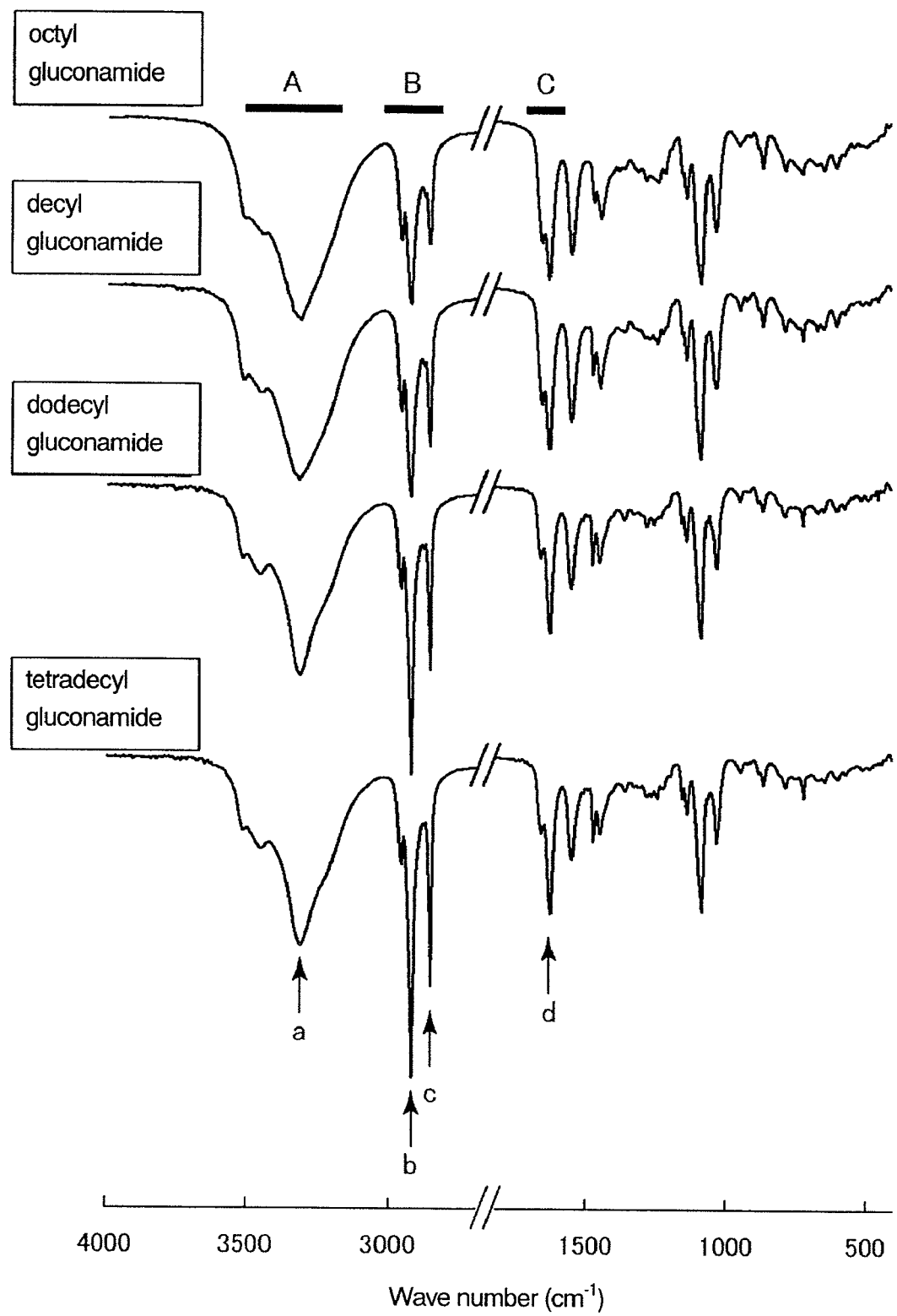
[Fig. 1]

[Fig. 2]
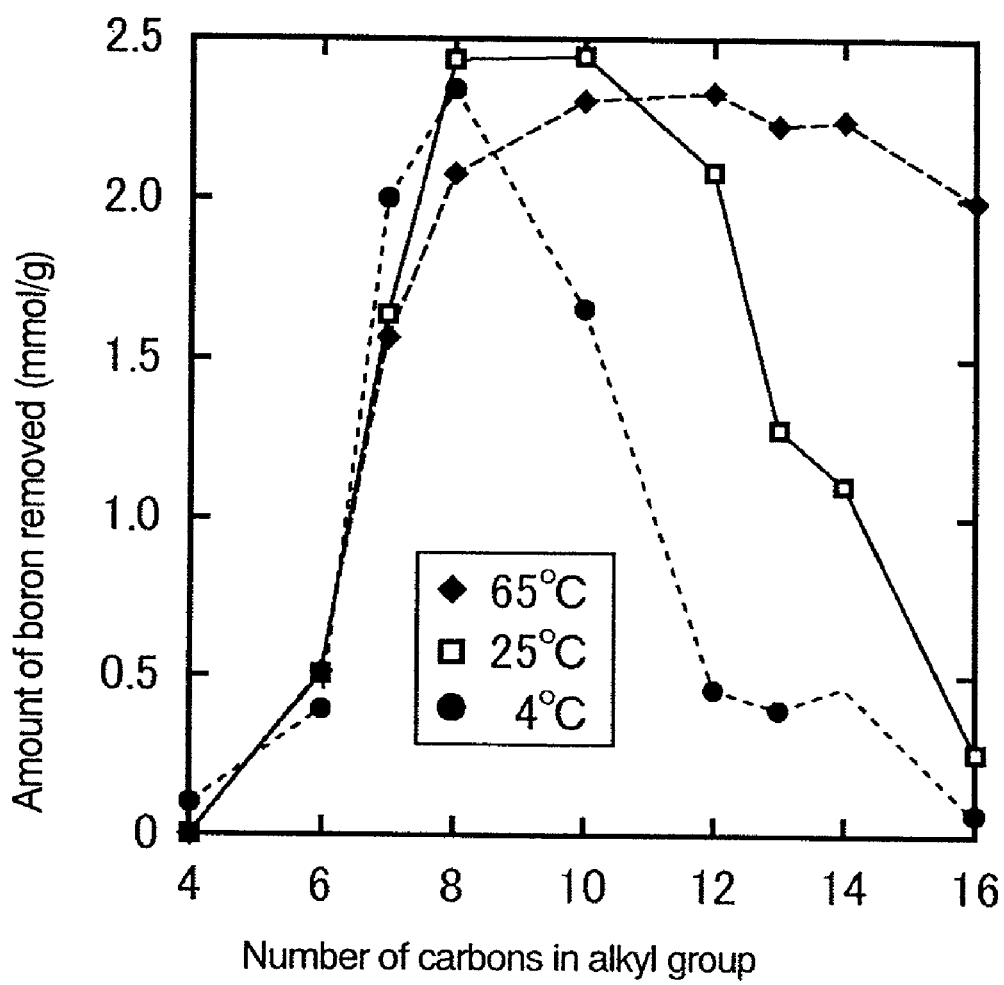

[Fig. 3]
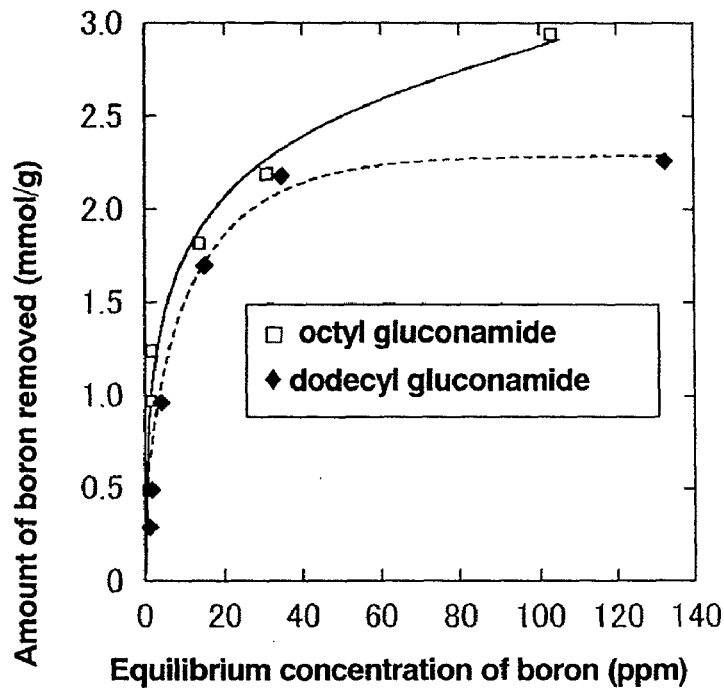
[Fig. 4]
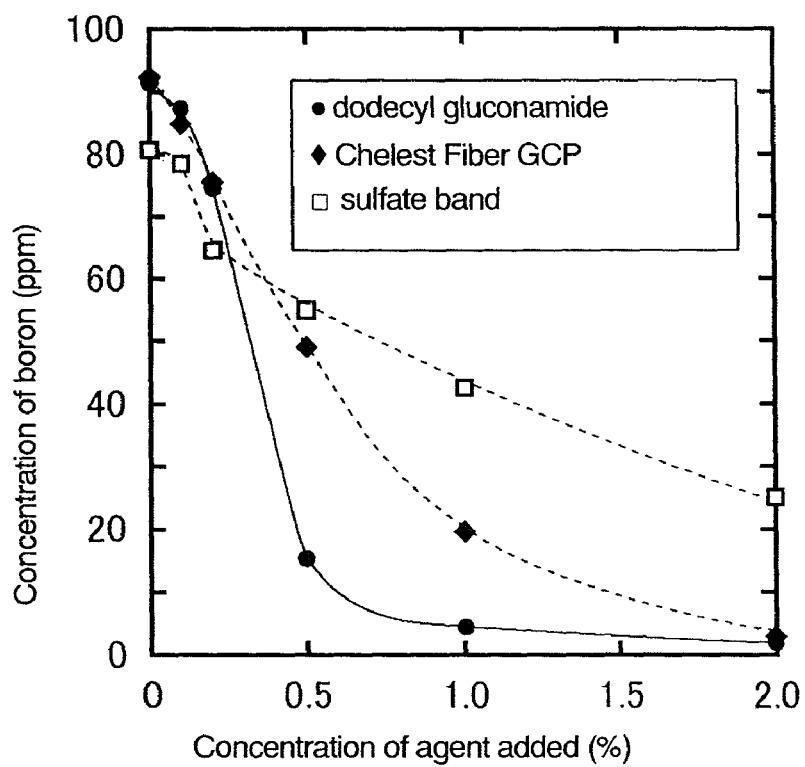

[Fig. 5]
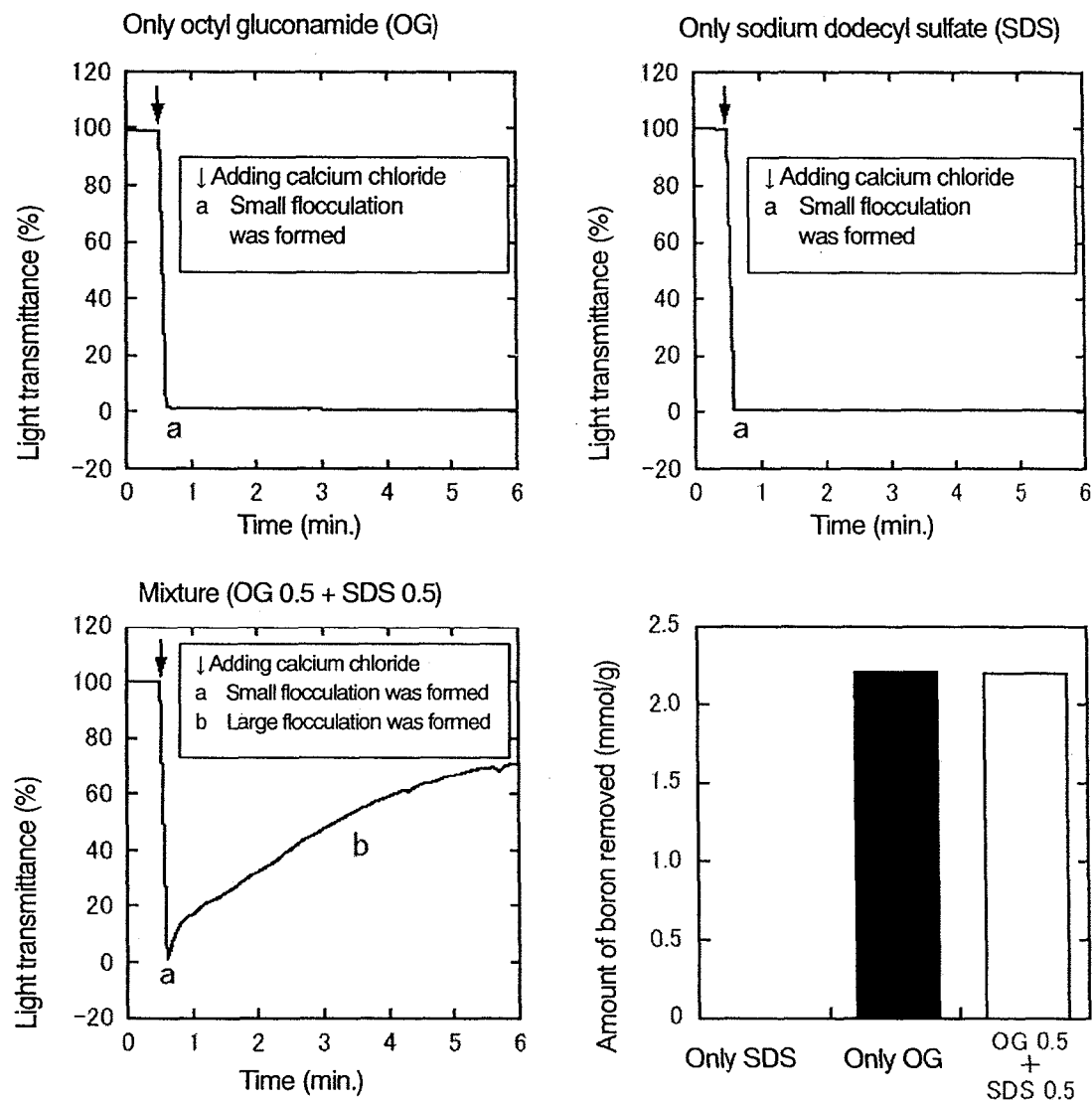

[Fig. 6]
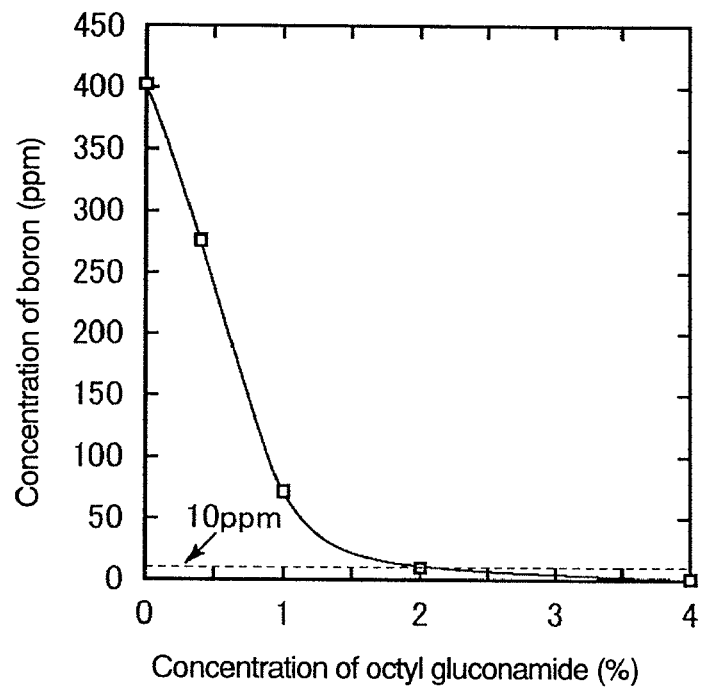
[Fig. 7]
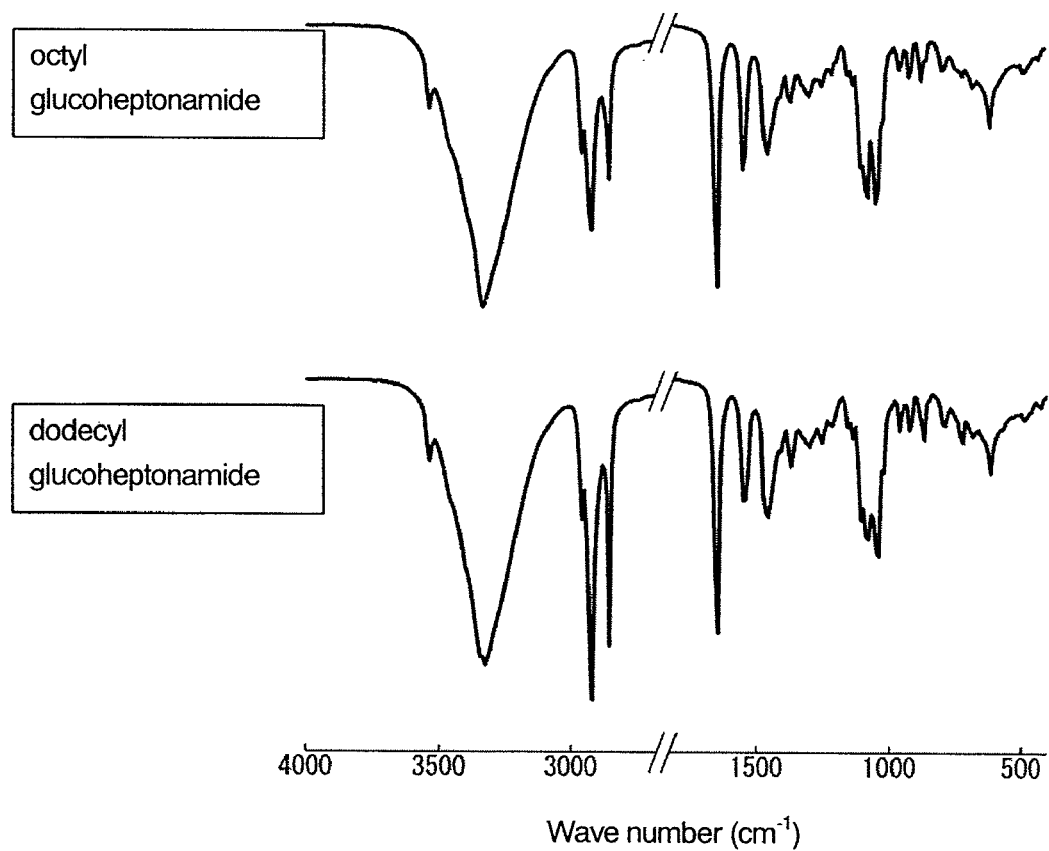

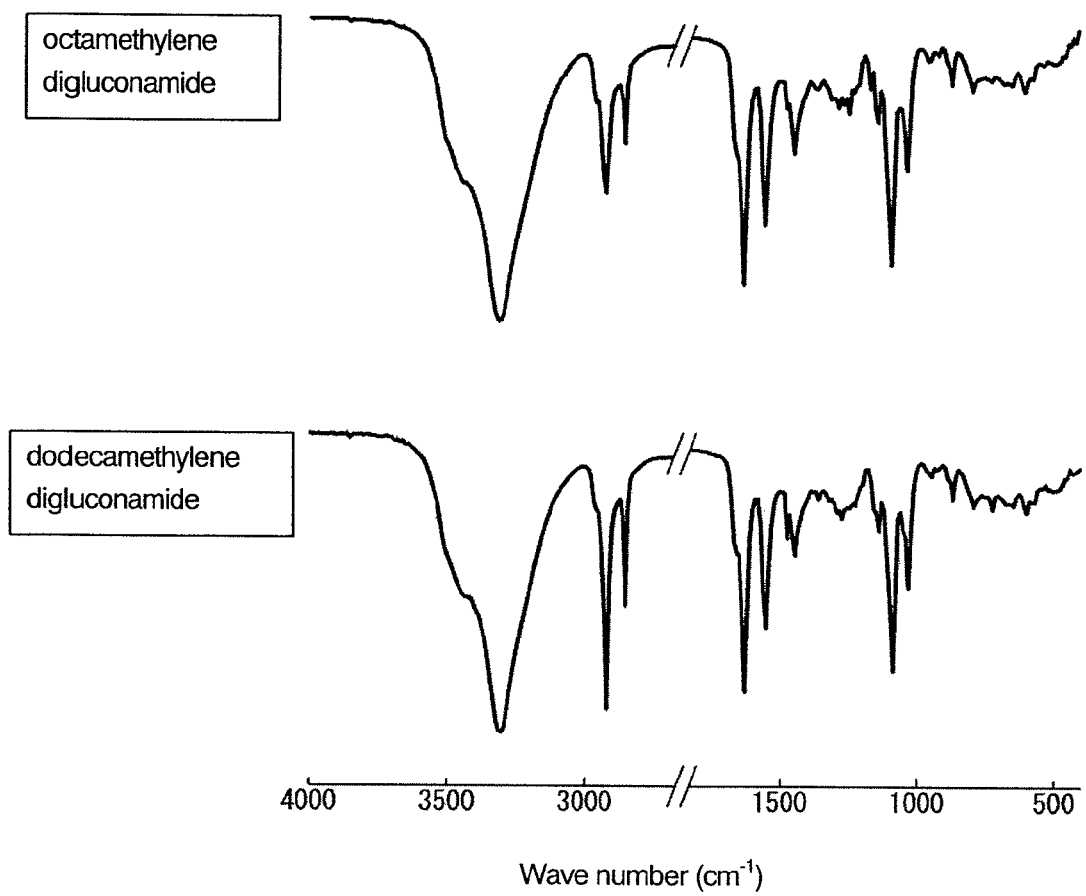
[Fig. 8]

[Fig. 9]
octamethylene diglucoheptonamide
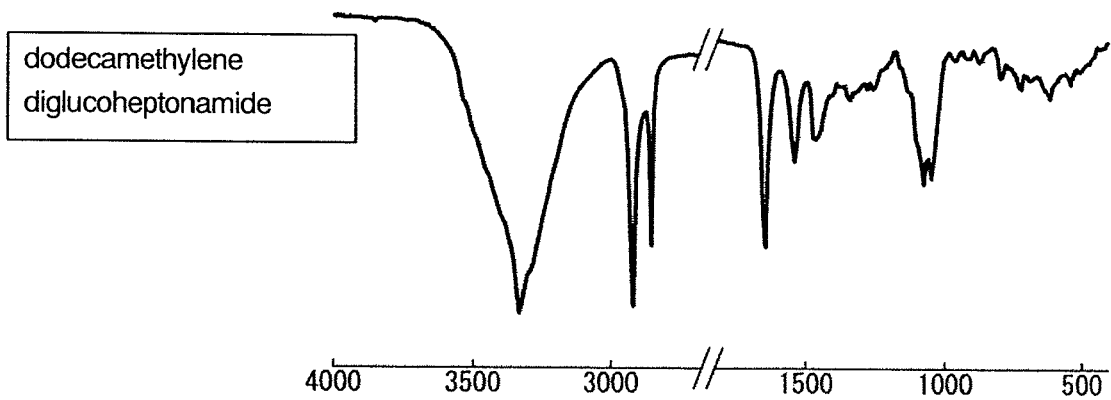
dodecamethylene diglucoheptonamide
Wave number (cm$^{-1}$)

BORON REMOVAL METHOD UTILIZING SUGAR AMIDE DERIVATIVE

CROSS-REFERENCE TO RELATED APPLICATIONS

This application is the U.S. National Phase under 35 U.S.C. §371 of International Application PCT/JP2008/059305, filed May 21, 2008, which was published in a non-English language, which claims priority to JP Application No. 2007-136436, filed May 23, 2007.

TECHNICAL FIELD

The present invention relates to a novel boron adsorbent for efficiently removing boron in a solution, a kit for removing boron, and a method of removing boron for removing boron from boron-containing water by utilizing the adsorbent and the kit.

BACKGROUND ART

A large amount of boron compounds are used in each of electroplating, enameled ironware, glaze, clay roof tile, and electrical component manufacturers, for example. Wastewater generated in the manufacturing process contains a high concentration of boric acid, borax, and the like. In accordance with the revision of the Water Pollution Prevention Law, an effluent standard value of boron, which has not been a subject to be regulated thus far, has been set to 10 ppm. Thus, there is a need for a technology that reduces the concentration of boron in boron-containing wastewater to a low concentration.

The methods of removing boron from boron-containing wastewater are broadly classified into a flocculation/precipitation method (batch method) using a flocculation/precipitation agent and an adsorption method (column method) using an adsorption resin, in the same manner as in methods of removing other heavy metals from water. For the former method, aluminum sulfate, which is inexpensive, is used. For the latter method, there are used a resin and a fiber each having an N-methyl glucamine group, for example.

It is an advantage of the flocculation/precipitation method that a large amount of boron-containing wastewater can be easily treated. Boron in wastewater can be removed by: adding a flocculation agent, a flocculation aid, a pH adjustor, and the like to an appropriate flocculation/precipitation vessel loaded with boron-containing wastewater, to thereby flocculate boron; and separating boron and water from each other by spontaneous precipitation or centrifugation. However, as the concentration of boron in wastewater becomes lower owing to the removal of boron, the flocculation to be formed decreases. Therefore, in order to reduce the concentration of boron to the effluent standard value or less, a large excess amount of flocculation agents must be added, which simultaneously generates a large amount of sludge and increases treatment cost. This has been a problem. Further, the flocculation rate is rate-limiting, and hence, a long retention time is required in a flocculation/precipitation vessel. This has been another problem.

On the other hand, it is an advantage of the adsorption method that the method involves, as an adsorption group, for example, N-methyl glucamine capable of specifically binding to a borate ion, and hence can reduce the concentration of boron to an extremely low concentration. However, N-methyl glucamine is expensive, and hence, an adsorbent using N-methyl glucamine causes an increase in treatment cost. In addition, in the adsorption method, the treatment of a large amount and a high concentration of boron-containing wastewater may saturate an adsorption group in a short time.

Therefore, in practice, a part of business sectors or companies that can afford to invest in treatment equipment have introduced a combination method involving: removing a majority of boron by such a flocculation/precipitation method as mentioned above; and then removing a low concentration of boron by the adsorption method.

In the above-mentioned background, there is a strong demand for the development of a boron adsorbent that exhibits an excellent boron adsorbing ability even in a low concentration of boron-containing water, is inexpensive, and has a high versatility, and a method of removing boron capable of simply and efficiently removing boron.

DISCLOSURE OF THE INVENTION

An object of the present invention is to provide a boron adsorbent that exhibits an excellent adsorbing ability against boron in a solution, is inexpensive, and has a high versatility, and a method of removing boron capable of simply and efficiently removing boron. In particular, an object of the present invention is to provide a boron adsorbent that exhibits an excellent adsorption rate and flocculation rate, and a method of removing boron capable of removing boron even from a low concentration of boron-containing water.

The inventor of the present invention has intensively studied in order to solve the above-mentioned problems. As a result, the inventor has found that an amide derivative with a particular structure has a high adsorbing ability against boron such as boric acid and borax present in a solution, in particular, has an ability to efficiently adsorb boron, even in a low concentration of boron-containing water. The inventor has further found that a complex of the amide derivative and boron flocculates by the addition of a cation having two or more valencies, and hence, boron can be easily removed from boron-containing water by separating the flocculate. The inventor has still further found that the treatment of boron-containing water with the amide derivative and an anionic surfactant makes stronger flocculation, which is formed by the addition of a cation having two or more valencies, and thus, boron can be separated from a solution in a highly efficient manner.

A first invention is a boron adsorbent containing an amide derivative represented by the following general formula (1).

General formula (1):

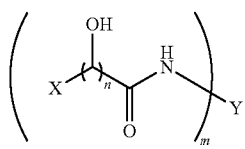

In the general formula (1): m represents 1 or 2; X represents —$CH_2OH$, —CHO, or —COOH; n represents an integer of 2 to 5; X are independent from each other and n are independent from each other when m represents 2; Y represents a monovalent hydrocarbon group having 6 to 16 carbon atoms when m represents 1, and represents a divalent hydrocarbon group having 8 to 18 carbon atoms when m represents 2; and X preferably represents —$CH_2OH$ and n preferably represents 4 or 5.

In addition, the boron adsorbent preferably further contains an anionic surfactant. The anionic surfactant is preferably a sulfonate surfactant or a sulfate surfactant.

A second invention is a kit for removing boron, including a combination of the boron adsorbent and a cation source having two or more valencies.

The cation source having two or more valencies is preferably at least one kind selected from the group consisting of an alkaline earth metal ion, an alkaline earth metal salt, a transition metal ion having two or more valencies, a transition metal salt having two or more valencies, a cationic polymer having two or more valencies, and a cationic polymer salt having two or more valencies.

A third invention is a method of removing boron, including, under an alkaline condition, adding the boron adsorbent to boron-containing water; and further adding a cation source having two or more valencies. Preferable aspects of the boron adsorbent and the cation source having two or more valencies are similar to those of the first and second invention.

A fourth invention is an amide derivative represented by the following general formula (2).

General formula (2):

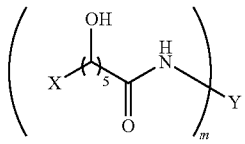

In the general formula (2): m represents 1 or 2; X represents —CH₂OH, —CHO, or —COOH; X are independent from each other when m represents 2; Y represents a monovalent hydrocarbon group having 6 to 16 carbon atoms when m represents 1, and represents a divalent hydrocarbon group having 8 to 18 carbon atoms when m represents 2; and X preferably represents a —CH₂OH group.

BRIEF DESCRIPTION OF THE DRAWINGS

FIG. 1 is a chart illustrating infrared absorption spectra of octylgluconamide, decylgluconamide, dodecylgluconamide, and tetradecyl gluconamide.

FIG. 2 is a graph illustrating a relationship between the number of carbons of an alkyl group in an alkyl gluconamide and an amount of boron removed, at each reaction temperature.

FIG. 3 is a graph illustrating adsorption isotherms of octyl gluconamide and dodecyl gluconamide.

FIG. 4 is a graph illustrating a comparison among an amount of boron removed by a method using dodecyl gluconamide, and amounts of boron removed by a flocculation/precipitation method using aluminum sulfate and a method using a commercially-available boron adsorbent, each of which is a conventional method.

FIG. 5 are graphs each illustrating a flocculate-forming process in mixing octyl gluconamide with sodium dodecyl sulfate.

FIG. 6 is a graph illustrating a relationship between an amount of octyl gluconamide added and a concentration of boron in industrial wastewater, in applying octyl gluconamide for purification of boron-containing industrial wastewater.

FIG. 7 is a chart illustrating infrared absorption spectra of octyl glucoheptonamide and dodecyl glucoheptonamide.

FIG. 8 is a chart illustrating infrared absorption spectra of octamethylene digluconamide and dodecamethylene digluconamide.

FIG. 9 is a chart illustrating infrared absorption spectra of octamethylene diglucoheptonamide and dodecamethylene diglucoheptonamide.

BEST MODE FOR CARRYING OUT THE INVENTION

A boron adsorbent of the present invention contains an amide derivative represented by the following general formula (1).

General formula (1):

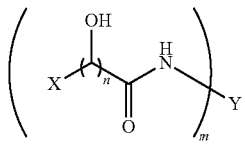

In the general formula (1), m represents 1 or 2.

When m represents 1: n represents an integer of 2 to 5 and preferably 4 or 5; X represents —CH₂OH, —CHO, or —COOH, and preferably —CH₂OH; Y represents a monovalent hydrocarbon group having 6 to 16 carbon atoms; the monovalent hydrocarbon group may be linear or branched and preferably linear; and the monovalent hydrocarbon group may be saturated or unsaturated and preferably saturated.

When m represents 2: n independently represent an integer of 2 to 5, at least one of n preferably represents 4 or 5, and both of n more preferably represent 4 or 5; X independently represent —CH₂OH, —CHO, or —COOH, at least one of X preferably represents —CH₂OH, and both of X more preferably represent —CH₂OH; Y represents a divalent hydrocarbon group having 8 to 18 carbon atoms; the divalent hydrocarbon group may be linear or branched and preferably linear; and the divalent hydrocarbon group may be saturated or unsaturated and preferably saturated.

The amide derivative represented by the general formula (1) may be produced by reacting a sugar lactone with an amine through ring-opening polymerization by a conventional method. The reaction is represented by the following formula:

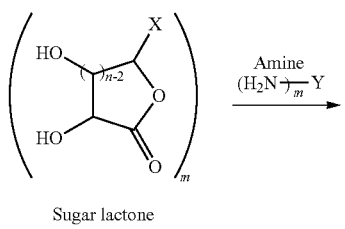

Sugar lactone

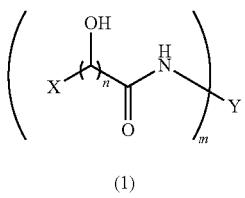

(1)

wherein X, Y, m, and n each have the same meaning as that in the general formula (1), provided that all m's represent the same number.

For example, in the presence of a solvent such as methanol or isopropyl alcohol, an amine and a sugar lactone as raw materials are stirred at a temperature ranging from room temperature to a boiling point of the solvent or lower. After a reaction for a predetermined period of time, the temperature of the solvent is lowered or an electrolyte is added, to thereby precipitate a reaction product. Thus, the amide derivative may be obtained.

Examples of the sugar lactone as a raw material include lactones of aldonic acid, uronic acid, aldaric acid, and the like.

Examples of the lactones of aldonic acid include erythronolactone, threonolactone, ribonolactone, arabinonolactone, xylonolactone, lyxonolactone, allonolactone, altronolactone, gluconolactone, mannolactone, gulonolactone, idonolactone, galactonolactone, talonolactone, alloheptonolactone, altroheptonolactone, glucoheptonolactone, mannoheptonolactone, guloheptonolactone, idoheptonolactone, galactoheptonolactone, and taloheptonolactone.

Examples of the lactones of uronic acid include riburonolactone, arabinuronolactone, xyluronolactone, lyxuronolactone, alluronolactone, altruronolactone, glucuronolactone, mannuronolactone, guluronolactone, iduronolactone, galacturonolactone, taluronolactone, allohepturonolactone, altrohepturonolactone, glucohepturonolactone, mannohepturonolactone, gulohepturonolactone, idohepturonolactone, galactohepturonolactone, and talohepturonolactone.

Examples of the lactones of aldaric acid include ribarolactone, arabarolactone, xylarolactone, lyxarolactone, allarolactone, altrarolactone, glucarolactone, mannarolactone, gularolactone, idarolactone, galactarolactone, talarolactone, alloheptarolactone, altroheptarolactone, glucoheptarolactone, mannoheptarolactone, guloheptarolactone, idoheptarolactone, galactoheptarolactone, and taloheptarolactone.

Of those sugar lactones: preferred are erythronolactone, gluconolactone, gulonolactone, mannolactone, glucoheptonolactone, glucuronolactone, and the like; more preferred are erythronolactone, gluconolactone, gulonolactone, and glucoheptonolactone; and most preferred are gluconolactone and glucoheptonolactone. Further, the amide derivative may be produced by using one kind of sugar lactone or may be produced by using a mixture of two or more kinds of sugar lactones.

When m represents 1, an example of the amine to serve as a raw material includes a monoamine having a hydrocarbon group having 6 to 16 carbon atoms. The hydrocarbon group may be linear or branched and preferably linear. Further, the hydrocarbon group may be saturated or unsaturated and preferably saturated. As the monoamine as a raw material, a linear alkylamine is preferred. In addition, the hydrocarbon group has preferably 7 to 16 and more preferably 7 to 13 carbon atoms.

Examples of the alkylamine include hexylamine, heptylamine, octylamine, nonylamine, decylamine, undecylamine, dodecylamine, tridecylamine, tetradecylamine, pentadecylamine, and hexadecylamine.

When m represents 2, an example of the amine to serve as a raw material includes a diamine having a hydrocarbon group having 8 to 18 carbon atoms. Positions of two amino groups are not particularly limited. The hydrocarbon group may be linear or branched and preferably linear. Further, the hydrocarbon group may be saturated or unsaturated and preferably saturated. As the diamine as a raw material, preferred is an alkylenediamine in which both ends of a linear alkane are substituted with an amino group. In addition, the hydrocarbon group preferably has 8 to 12 carbon atoms.

Examples of the alkylenediamine include octamethylenediamine, nonamethylenediamine, decamethylenediamine, undecamethylenediamine, dodecamethylenediamine, tridecamethylenediamine, tetradecarnethylenediamine, pentadecamethylenediamine, hexadecamethylenediamine, heptadecamethylenediamine, and octadecamethylenediamine.

The molar fraction of the sugar lactone to the monoamine having a hydrocarbon group having 6 to 16 carbon atoms is preferably 0.1 to 10 mol and more preferably 0.5 to 2 mol of the monoamine with respect to 1 mol of the sugar lactone. Further, the molar fraction of the sugar lactone to the diamine having a hydrocarbon group having 8 to 18 carbon atoms is preferably 0.05 to 5 mol and more preferably 0.25 to 1 mol of the diamine with respect to 1 mol of the sugar lactone.

The synthesis reaction may be performed by adding the amine to a solution obtained by dissolving in advance the sugar lactone in an appropriate solvent such as dimethyl sulfoxide or heated methanol or ethanol. If required, the synthesis reaction may also be performed by directly loading the sugar lactone into the amine diluted with a solvent such as methanol or ethanol. In this case, the amount of the solvent is preferably an equivalent amount to a 30-fold amount with respect to the mass of the amine to be reacted. The reaction temperature is preferably $-20°$ C. to $150°$ C. and more preferably $0°$ C. to $100°$ C. The reaction time is preferably 30 seconds to 24 hours and more preferably 5 minutes to 8 hours.

The reaction is performed in the above-mentioned manner, thereby affording a product containing the amide derivative as an essential component of the boron adsorbent of the present invention. The amide derivative is precipitated by appropriately cooling the obtained product in the solution. The temperature at which the amide derivative is precipitated varies depending on a carbon chain length of the amine as a raw material, which is preferably $-20°$ C. to $80°$ C. and more preferably $-20°$ C. to $40°$ C.

Subsequently, the resulting precipitate is filtered off. If required, the precipitate may be sufficiently washed with a solvent such as methanol or ethanol for dissolving the amine as a raw material, for the purpose of removing an unreacted amine, and may be sufficiently washed with water to hydrolyze an unreacted sugar lactone into aldonic acid, uronic acid, or aldaric acid, which is dissolved in water, for the purpose of removing the unreacted sugar lactone. In addition, the compound obtained by filtration may be dissolved in hot water, cooled again, recrystallized, filtered, and then dissolved in a solvent such as heated methanol or ethanol, followed by recrystallization with cooling. In some cases, in order to increase purity, the above-mentioned operation may be repeatedly performed. The purification product of the amide derivative, which is obtained by appropriately performing purification in the above-mentioned manner, may be dried and then used as an essential component of the boron adsorbent of the present invention.

The amide derivative thus obtained adsorbs boron such as boric acid and borax through an adsorption site formed of a functional group represented by X in the general formula (1) and a hydroxy group adjacent to the functional group. Thus, the amide derivative forms a complex with boron.

The boron adsorbent of the present invention may contain only one kind of the amide derivatives, or may contain two or more kinds of the amide derivatives in combination.

The boron adsorbent of the present invention preferably further contains an anionic surfactant in addition to the amide derivative. This is because the use of the amide derivative and the anionic surfactant in combination makes bigger and stronger flocculation, which is formed by the addition of such a cation source having two or more valencies described below. This is probably because water repulsion is synergistically enhanced in flocculating the complex of the amide derivative and boron by using a cation having two or more valencies. Further, the anionic surfactant also serves as a dispersant for the amide derivative when using the boron adsorbent of the present invention. In particular, when the boron adsorbent has a dosage form such as a gel, a wax solid, or a powder, the anionic surfactant is preferably incorporated.

The anionic surfactant contained in the boron adsorbent of the present invention may be any as long as it supports the flocculation of the complex of the amide derivative and boron by the addition of a cation having two or more valencies described below. Examples of the anionic surfactant include: a higher alkyl sulfate such as sodium dodecyl sulfate and potassium dodecyl sulfate; an alkyl ether sulfate such as triethanolamine polyoxyethylene dodecyl sulfate and sodium polyoxyethylene dodecyl sulfate; an N-acyl glycinate such as sodium N-dodecanoyl-N-methyl glycinate; a higher fatty acid amide sulfonate such as sodium N-tetradecanoyl-N-methyl taurate, sodium coconut oil fatty acid methyl tauride, and sodium dodecyl methyl tauride; a sulfosuccinate such as sodium di-2-ethylhexyl sulfosuccinate, sodium monododecanoyl monoethanolamide polyoxyethylene sulfosuccinate, and sodium dodecanoyl polypropyleneglycol sulfosuccinate; an alkyl benzene sulfonate such as sodium dodecyl benzene sulfonate, triethanolamine dodecyl benzene sulfonate, and dodecyl benzene sulfonic acid; an N-acyl glutamate such as monosodium N-dodecanoyl glutamate, disodium N-octadecanoyl glutamate, and monosodium N-tetradecanoyl-L-glutamate; a higher fatty acid ester sulfate such as sodium hydrogenated coconut oil fatty acid glycerin sulfate; a sulfated oil such as Turkey red oil; α-olefin sulfonate; a higher fatty acid ester sulfonate; a secondary alcohol sulfate; a higher fatty acid alkylolamide sulfate; alkanoyl monoethanolamide succinate such as sodium dodecanoyl monoethanolamide succinate; and ditriethanolamine N-hexadecanoyl aspartate.

Of those, preferred are: a sulfonate anionic surfactant, which has a hydrophilic group of —$SO_3^-$, such as sodium di-2-ethylhexyl sulfosuccinate, sodium monododecanoyl monoethanolamide polyoxyethylene sulfosuccinate, sodium dodecanoyl polypropyleneglycol sulfosuccinate, sodium dodecyl benzene sulfonate, and triethanolamine dodecyl benzene sulfonate; and a sulfate anionic surfactant, which has a hydrophilic group of —$OSO_3^-$, such as sodium dodecyl sulfate (SDS), potassium dodecyl sulfate, sodium polyoxyethylene dodecyl sulfate, sodium hydrogenated coconut oil fatty acid glycerin sulfate, a sulfated oil such as Turkey red oil, sodium secondary alcohol sulfate, and sodium higher fatty acid alkylolamide sulfate.

Further, preferably, there is not used such an anionic surfactant that the anionic surfactant itself prevents the flocculation of the complex of the amide derivative and boron by forming an insoluble matter with the cation having two or more valencies, in the presence of the complex of the amide derivative and boron, and the cation having two or more valencies.

The boron adsorbent of the present invention may contain only one kind of the anionic surfactants, or may contain two or more kinds of the anionic surfactants in combination. Further, in the boron adsorbent of the present invention, the content of the anionic surfactant is preferably 1/1,000 to 10 mol-fold and more preferably 1/100 to 5 mol-fold with respect to the amide derivative. The content of the anionic surfactant is also preferably 0.0008 to 8 mass-fold and more preferably 0.008 to 4 mass-fold with respect to the amide derivative, for example.

The form of the boron adsorbent of the present invention is not particularly limited. Examples of the form include an aqueous solution, a solution obtained by using an appropriate solvent, a gel, a wax solid, and a powder. It is an advantage of the solution that each of the components goes rapidly across boron-containing water, and thus, a high reactivity is obtained. It is an advantage of the gel, the wax solid, and the powder that they are convenient from the viewpoint of transportation or storage. When the boron adsorbent is formed into a powder, processing may be performed to enhance the solubility.

Further, as long as the action of each of the components is not impaired, the boron adsorbent of the present invention may also contain other components. For example, a dispersant, a solubilizing agent, or a wetting agent may also be incorporated for the purpose of promoting the dissolution of the boron adsorbent into boron-containing water.

The boron adsorbent of the present invention may be formed into a kit for removing boron by further combining the cation source having two or more valencies. The term "cation source" as used herein refers to a substance, at least one part of which is dissolved in water to supply a cation.

The addition of the cation source having two or more valencies to boron-containing water causes the flocculation of the complex of the amide derivative and boron.

The cation source having two or more valencies may be any as long as it ionizes in water to supply a cation having two or more valencies. The cation source may be a cation itself, a substance that is easily dissolved in water to ionize, or a substance that has a low solubility in water and ionizes in part.

Examples of the cation source include: a cation such as an alkaline earth metal ion and a transition metal ion having two or more valencies; a metal salt such as an alkaline earth metal salt and a transition metal salt having two or more valencies; and a hydrate thereof; and a cationic polymer. Specific examples of the cation include a calcium ion, a magnesium ion, and a barium ion, and a metal ion such as an iron ion, an aluminum ion, and a manganese ion.

Further, examples of the metal salt include calcium acetate, calcium bromide, calcium carbonate, calcium chloride, calcium citrate, calcium dihydrogen diphosphate, calcium dihydrogen phosphate, calcium dihydrogen pyrophosphate, calcium diphosphate, calcium fluoride, calcium hydrogen phosphate, calcium hydroxide, calcium hypophosphite, calcium lactate, calcium monohydrogen phosphate, calcium nitrate, tricalcium phosphate, calcium phosphite, calcium silicate, calcium sulfate, calcium thiosulfate, magnesium acetate, magnesium bromide, magnesium carbonate, magnesium chloride, magnesium citrate, magnesium fluoride, magnesium hydrogen phosphate, magnesium hydroxide, magnesium lactate, magnesium nitrate, magnesium (II) phosphate, magnesium (III) phosphate, magnesium potassium chloride, magnesium pyrophosphate, magnesium sulfate, magnesium thiosulfate, magnesium silicate, barium acetate, barium bromide, barium carbonate, barium chloride, barium fluoride, barium hydrogen phosphate, barium hydroxide, barium lactate, barium metaphosphate, barium nitrate, barium sulfate, barium thiosulfate, barium silicate, iron (II) acetate, iron (III) ammonium citrate, iron (III) ammonium oxalate, iron (II) ammonium sulfate, iron (III) ammonium sulfate, iron (II) chloride, iron (III) chloride, iron (II) bromide, iron (III) bromide, iron (III) citrate, iron (III) diphosphate, iron disulfide, iron (III) hydroxide, iron (III) nitrate, iron (III) phosphate, iron (II) sulfate, iron (III) sulfate, aluminum acetate, aluminum ammonium sulfate, aluminum bromide, aluminum carbonate, aluminum (III) chloride, aluminum fluoride, aluminum hydroxide, aluminum lactate, aluminum metaphosphate, aluminum nitrate, aluminum phosphate, aluminum potassium sulfate, aluminum sodium sulfate, aluminum silicate, aluminum sulfate, manganese (II) acetate, manganese (III) acetate, manganese (II) ammonium sulfate, manganese (II) bromide, manganese (II) carbonate, manganese (II) chloride, manganese (III) flouride, manganese (II) nitrate, manganese (III) phosphate, manganese (II) phosphate, and manganese (II) sulfate.

In addition, examples of a water-soluble cationic polymer include polyethyleneamine, polyethyleneimine, polyvinylamine, polyallylamine, polyvinylpyridine, polydiallylamine acrylic amide, polydiallyl dimethyl ammonium salt, polydimethyl aminoethyl methacrylate, and poly(N-methylpyridinium-2-yl)acetylene.

Of those, preferred are: metal salts such as calcium acetate, calcium carbonate, calcium chloride, calcium hydroxide, calcium nitrate, calcium sulfate, calcium thiosulfate, magnesium acetate, magnesium carbonate, magnesium chloride, magnesium hydroxide, magnesium nitrate, magnesium sulfate, magnesium thiosulfate, barium acetate, barium carbonate, barium chloride, barium hydroxide, barium nitrate, barium sulfate, barium thiosulfate, iron (II) acetate, iron (II) ammonium sulfate, iron (III) ammonium sulfate, iron (II) sulfate, iron (III) sulfate, aluminum acetate, aluminum ammonium sulfate, aluminum nitrate, aluminum potassium sulfate, aluminum sodium sulfate, aluminum sulfate, manganese (II) acetate, manganese (III) acetate, manganese (III) nitrate, manganese (III) ammonium sulfate, manganese (II) carbonate, manganese (II) chloride, manganese (II) nitrate, and manganese (II) sulfate, and a hydrate thereof; and a water-soluble cationic polymer such as polyethyleneimine, a polydiallyl dimethyl ammonium salt, and polyallylamine.

The kit for removing boron of the present invention may contain only one kind of the cation source having two or more valencies, or may contain two or more kinds of the cation sources in combination.

In the kit for removing boron of the present invention, the content of the cation source having two or more valencies is preferably 0.1 to 1,000 fold and more preferably 1 to 500 fold with respect to the amide derivative at a molar ratio.

Further, in the kit for removing boron of the present invention, the form of the cation source having two or more valencies is, but is not particularly limited thereto, preferably a form such as a powder, an aqueous solution, or a porous tablet.

As described below, in order to remove boron efficiently, the cation source having two or more valencies is preferably added after the amide derivative has adsorbed boron, and hence has a form packaged separately from both of the amide derivative and the anionic surfactant.

Meanwhile, when the boron adsorbent is free of any anionic surfactant, the kit for removing boron of the present invention may be made by packaging the anionic surfactant separately from the amide derivative and the cation source having two or more valencies.

The method of removing boron of the present invention includes, under an alkaline condition, adding the boron adsorbent of the present invention to boron-containing water and further adding the cation source having two or more valencies. The pH is preferably 7 to 14 and more preferably 8 to 13. In the method of removing boron of the present invention, the stage of adjusting the pH of boron-containing water is not particularly limited. However, preferred are: a method involving adding the boron adsorbent of the present invention to boron-containing water, the pH of which had been adjusted in advance, and subsequently adding a cation source having two or more valencies; and a method involving adding the boron adsorbent of the present invention to boron-containing water, thereafter adjusting the pH of the aqueous solution, and subsequently adding the cation source having two or more valencies.

For example, the pH of the aqueous solution optimal for binding the boron adsorbent of the present invention to boron in boron-containing water is preferably 3 to 14 and more preferably 5 to 13. Therefore, when the boron adsorbent is added to boron-containing water under the above-mentioned condition to adsorb boron to the amide derivative, and then the pH of the boron-containing water is adjusted to 7 to 14 and preferably 8 to 13, boron that adsorbed to the amide derivative turns into its anion. Thus, as described below, the coexistence of the cation having two or more valencies may cause the ionicity to disappear, and cause the flocculation.

The method of adding the boron adsorbent of the present invention is not particularly limited as long as the method can bring the amide derivative and the anionic surfactant contained in the boron adsorbent into contact with boron-containing water so that those components might exert their respective actions. Examples thereof include: a method of adding the boron adsorbent of the present invention to boron-containing water and stirring; a method of loading or fixing the boron adsorbent into a circulation vessel and circulating boron-containing water, the pH of which has been adjusted to an alkaline pH; and a method of loading or fixing the boron adsorbent into a circulation vessel and circulating boron-containing water.

Further, it is envisaged that: when the boron adsorbent of the present invention is a gel or a wax solid, a mass, of which the surface only is dissolved and the interior is not dissolved, is formed; and when the boron adsorbent is a powder, the dispersion is not performed well owing to the formation of a lump of powder, for example. In such a case, a dispersant or a solubilizing agent may be appropriately added, for example.

Further, the temperature of the boron-containing water when adding the boron adsorbent is, but is not limited to, preferably 0 to 100° C.

The cation source having two or more valencies is added after the addition of the boron adsorbent to boron-containing water and the adsorption of boron to the amide derivative. Further, the cation source having two or more valencies may be added either before or after the adjustment of the pH to an alkaline condition. Under the alkaline condition, boron, which is bound to the amide derivative, turns into its anion, and hence the cation having two or more valencies binds to the anion, thereby causing the ionicity of boron to disappear. In addition, a hydrophobic functional group of the amide derivative is arranged on the outside, and the complex of the amide derivative and boron flocculates with another complex through a hydrophobic site in an aqueous solution.

The addition amount of the cation source having two or more valencies is preferably 1/1,000 to 100 mol-fold and more preferably 1/100 to 10 mol-fold with respect to the complex of the amide derivative and boron.

The formed flocculation may be separated from water by filtration with a filter material or centrifugation. Also, the flocculation may be easily dehydrated by further press with a pressing machine and subjected to incineration treatment.

Further, the method of removing boron of the present invention may be performed in combination with an existing method of removing boron by flocculation/precipitation using aluminum sulfate and slaked lime, and a method of removing boron using a methyl glucamine resin, or a boron adsorbent obtained by binding a methyl glucamine group to a cellulosic substrate. The method of removing boron of the present invention may be performed in parallel with the existing method of removing boron. Further, the method of removing boron of the present invention may be performed after the existing method of removing boron. Still further, the method of removing boron of the present invention may be performed before the existing method of removing boron.

EXAMPLES

Hereinafter, the present invention is specifically described by way of examples. However, the present invention is not limited to those examples.

<Measurement Example of Amount of Boron Removed>

The amount of boron removed was measured by the following measurement method.

10 g of an amide derivative and 10 g of sodium dodecyl sulfate were sufficiently mixed by trituration in a mortar. 0.6 g of the powder (the weight of the amide derivative: W=0.3 g) was added to a solution obtained by mixing 10 mL of a boron solution prepared so as to have the concentration of boric acid of 1,000 mg/L with 80 mL of water, followed by sufficient stirring for 10 minutes. The resulting solution was adjusted so as to have a pH of 9.3 by adding a 10 mol/L sodium hydroxide aqueous solution. Water was further added to the solution so that the total volume might be 97 mL. The solution was sufficiently stirred for 30 minutes so that the amide derivative might sufficiently react with boric acid in the solution. Next, 3 mL of a 1 mol/L calcium chloride aqueous solution were added (the total volume of the solution: V=0.1 L) and the whole was sufficiently stirred for 30 minutes so that the flocculation might be sufficiently formed. Parts (10 mL) of the boron solution was taken and centrifuged to precipitate a flocculate. Then, the supernatant was recovered and used as a specimen. The concentration of boron in the specimen was calculated by performing an absorbance measurement in accordance with an azomethine H method. That is, 0.1 mL of the recovered specimen was added to 7.9 mL of water, and to the resultant, 1 mL of an azomethine H solution (50 mg of azomethine H and 150 mg of ascorbic acid were dissolved in water so that the volume might be 5 mL) and 1 mL of a buffer (5 g of ammonium acetate, 0.3 mL of sulfate, 0.125 mL of a 85% phosphoric acid, 20 mg of citric acid monohydrate, and 20 mg of ethylenediamine tetraacetate disodium salt were added to 5 mL of water and dissolved with heating) were added so that the total volume might be 10 mL and the whole was sufficiently stirred, followed by a reaction at room temperature for 1 hour. After that, the absorbance ($ABS_s$) at 410 nm was measured with a spectrophotometer. Similarly, the absorbance ($ABS_0$) of a sample free of boric acid and the absorbance ($ABS_{100}$) of a sample containing 100 mg/L boric acid were also measured after the reaction with azomethine H. The concentration of boron (B) in the specimen and the amount of boron removed (Ad) by the amide derivative are calculated with the following expressions by using the total volume (V=0.1 L) of the reaction solution, the weight (W=0.3 g) of the amide derivative in the reaction solution, and the atomic weight of boron ($AW_B$=10).

$$B=(ABS_s-ABS_0)/(ABS_{100}-ABS_0)\times 100 \text{ (mg/L)}$$

$$Ad=(100-B)/W\times V/AW_B$$

This is only illustrative of the measurement of the amount of boron removed. In the following examples, depending on purposes or needs, the concentration of the boron solution, the amount of the amide derivative added, or the temperature at which the boron solution and the amide derivative are reacted with each other is modified. However, the respective differences do not affect the quality of a method of evaluating an adsorbing ability of the amide derivative in any way.

Example 1

(1) Predetermined amounts (0.28 mol) according to Table 1 of various alkylamines, in which a hydrogen atom at one end of a linear alkane having 4 to 16 carbon atoms was substituted with an amino group, were each added into 300 mL of methanol, and the whole was stirred and dissolved in a hot water bath (50° C.). Added to the resultant were 50.0 g (0.28 mol) of gluconolactone powder to perform a reaction. In this case, gluconolactone rapidly reacted with each of the alkylamines according to Table 1, and as the reaction proceeded, the powder disappeared and a white condensate was observed. In order to reliably complete the reaction, the reaction was continued in a hot water bath for additional 30 minutes.

After that, the reaction solution was cooled by being left to stand in ice water for the purpose of sufficiently precipitating a crystal of the condensate. Then, the crystal was recovered. The recovered crystal was dissolved in hot water at 90° C. and then cooled again by being left to stand in ice water for the purpose of achieving sufficient recrystallization. Then, the crystal was recovered, further dissolved in methanol heated to 60° C., and subsequently cooled again by being left to stand in ice water for the purpose of achieving sufficient recrystallization of the condensate. Thus, the precipitated crystal was recovered. After the recrystallization operation was performed twice in total, an authentic sample was obtained by drying at 60° C. overnight.

Further, predetermined amounts (0.14 mol) according to Table of octamethylenediamine (having 8 carbon atoms) and dodecamethylenediamine (having 12 carbon atoms), each of which was one of the alkylenediamines in which hydrogen atoms at both ends of an linear alkane were each substituted with an amino group, were each added into 300 mL of methanol, and the whole was stirred and dissolved in a hot water bath (50° C.). Added to each of the resulting solutions were 50.0 g of gluconolactone powder (0.28 mol) to perform a reaction. In this case, gluconolactone rapidly reacted with each of the above-mentioned alkylenediamines, and as the reaction proceeded, the powder disappeared. The reaction time was about 5 minutes. As two molecules of gluconolactone reacted with one molecule of those alkylenediamines by ring-opening polymerization, two amino groups of the alkylenediamines were each converted to an amide, which led to the reduction in the solubility in methanol. As a result, the precipitation occurred and a white condensate was observed. In order to reliably complete the reaction, the reaction was continued in a hot water bath for additional 30 minutes.

After that, the reaction solution was cooled by being left to stand in ice water for the purpose of sufficiently precipitating a crystal of the condensate. Then, the crystal was recovered. The recovered crystal was dissolved in hot water at 90° C., and cooled again by being left to stand in ice water for the purpose of achieving sufficient recrystallization. Then, the crystal was recovered, further dissolved in methanol heated to 60° C., and then cooled again by being left to stand in ice water for the purpose of achieving sufficient recrystallization of the condensate. Thus, the precipitated crystal was recovered. After the recrystallization operation was performed twice in total, an authentic sample was obtained by drying at 60° C. overnight.

Table 1 shows the yield (weight), the properties of the obtained crystal, and the amount of boron removed at room temperature (25° C.) of each of the compounds.

TABLE 1

| Kind of alkylamine (number of carbons) | Molecular weight | Amount added (g) | Yield of authentic sample (g) | Properties of crystal | Amount of boron removed (mmol/g) |
| --- | --- | --- | --- | --- | --- |
| Butylamine (4) | 73.1 | 20.5 | 21.2 | White powder | 0.0 |
| Hexylamine (6) | 101.2 | 28.4 | 39.2 | White powder | 0.5 |
| Heptylamine (7) | 115.2 | 32.3 | 59.3 | Shiny white powder | 1.6 |
| Octylamine (8) | 129.2 | 36.3 | 68.2 | Shiny white powder | 2.4 |
| Decylamine (10) | 157.3 | 44.2 | 78.2 | Shiny white powder | 2.5 |
| Dodecylamine (12) | 185.4 | 52.0 | 91.8 | Shiny white powder | 2.1 |
| Tridecylamine (13) | 199.4 | 56.0 | 96.5 | Shiny white powder | 1.3 |
| Tetradecylamine (14) | 213.4 | 59.9 | 102.2 | Shiny white powder | 1.1 |
| Hexadecylamine (16) | 241.5 | 67.7 | 113.0 | Shiny white powder | 0.3 |
| Octamethylenediamine (8) | 144.3 | 20.2 | 59.1 | Shiny white powder | 0.2 |
| Dodecamethylenediamine (12) | 200.4 | 28.1 | 74.9 | Shiny white powder | 2.6 |

In the alkyl gluconamide obtained by using the alkylamine as a raw material, when the alkyl group had 6 or more carbon atoms, a boron removing ability was observed. Further, in the alkylene digluconamide obtained by using the alkylenediamine as a raw material, when the alkylene group had 8 or more carbon atoms, a boron removing ability was observed.

(2) 10.4 g (0.056 mol) of dodecylamine were diluted with methanol so that the total volume might be 60 mL, and the whole was stirred in a hot water bath (50° C.). To the resultant, predetermined amounts (0.056 mol) according to Table 2 of various sugar lactone powders were each added, followed by a reaction with stirring. Various sugar lactones in a form of powder according to Table 2 each rapidly reacted with dodecylamine, and as the reaction proceeded, the powder disappeared.

In this case, when erythronolactone (sugar having 4 carbon atoms), gluconolactone or gulonolactone (sugar having 6 carbon atoms), or glucoheptonolactone (sugar having 7 carbon atoms), which was one of the lactones of aldonic acid, was subjected to ring-opening polymerization with dodecylamine, the compound was precipitated to afford a shiny white condensate. After that, the reaction solution was cooled by being left to stand in ice water for the purpose of sufficiently precipitating a crystal of the condensate. Then, the crystal was recovered. The recovered crystal was dissolved in hot water at 90° C. and then cooled again by being left to stand in ice water for the purpose of achieving sufficient recrystallization. Then, the crystal was recovered, further dissolved in methanol heated to 60° C., and then cooled again by being left to stand in ice water for the purpose of achieving sufficient recrystallizion of the condensate. Thus, the precipitated crystal was recovered. After the recrystallization operation was performed twice in total, an authentic sample was obtained by drying at 60° C. overnight.

On the other hand, when glucuronolactone (sugar having 6 carbon atoms), which was one of the lactones of uronic acid, was subjected to ring-opening polymerization with dodecylamine, the compound did not precipitate but turned into a yellowish brown solution. When the solution was suspended in a large amount (5 L) of water, the solution became opaque, the color of which was yellowish white. Therefore, by adding 6 g of salt to the resulting solution, the opaque product was recovered by salting-out. The resulting product was suspended again in a large amount (5 L) of water, and the opaque product was recovered by salting-out with the addition of 6 g of salt. In addition, the resulting product was suspended in a small amount (0.1 L) of water and then centrifuged to precipitate and recover a suspended solid, followed by drying at 60° C. overnight. Thus, an authentic sample was obtained.

In addition, when glucarolactone (sugar having 6 carbon atoms), which was one of lactones of the aldaric acid, was subjected to ring-opening polymerization with dodecylamine, the compound did not precipitate and turned into a pale yellowish solution. Added to the resulting solution were 500 mL of water and 10 mL of a 1 mol/L calcium chloride aqueous solution, followed by stirring. As a result, the compound flocculated. Therefore, the compound was precipitated by centrifugation to remove the supernatant. To the resultant, 50 mL of methanol and 150 mL of water were added. After that, the whole was sufficiently suspended and then centrifuged again to remove the supernatant. The washing operation including the precipitation and the removal of the supernatant was performed twice in total, and the recovered precipitation was dried at 60° C. overnight to afford an authentic sample.

Table 2 shows the yield (weight), the properties of the obtained crystal, and the amount of boron removed at room temperature (25° C.) of each of the compounds.

TABLE 2

| Kind of sugar lactone | Molecular weight | Amount added (g) | Yield of authentic sample (g) | Properties of crystal | Amount of boron removed (mmol/g) |
|---|---|---|---|---|---|
| Erythronolactone | 118.1 | 6.6 | 11.5 | Shiny white powder | 1.5 |
| Gluconolactone | 178.1 | 10.0 | 18.4 | Shiny white powder | 2.3 |
| Gulonolactone | 178.1 | 10.0 | 18.6 | Shiny white powder | 2.0 |
| Glucoheptonolactone | 208.2 | 11.7 | 18.0 | Shiny white powder | 2.3 |
| Glucuronolactone | 176.1 | 9.9 | 10.7 | Orangish white powder | 1.5 |
| Glucarolactone | 192.1 | 10.8 | 3.6 | Pale yellowish white powder | 0.3 |

Even in the case where any sugar lactone as a raw material was used, a dodecyl amide derivative exhibited a boron adsorbing ability. In particular, when the dodecyl amide derivative obtained by using gluconolactone, gulonolactone, or glucoheptonolactone was used as a raw material, an extremely large amount of boron removed was exhibited.

(3) Gluconolactone was used as the above-mentioned lactone of aldonic acid and reacted with each of octylamine, decylamine, dodecylamine, and tetradecylamine. The resulting amide derivatives, that is, octylgluconamide, decylgluconamide, dodecyl gluconamide, and tetradecyl gluconamide were measured for their melting points as described below.

| | |
|---|---|
| Octyl gluconamide: | 158° C. |
| Decyl gluconamide: | 156° C. |
| Dodecyl gluconamide: | 157° C. |
| Tetradecyl gluconamide: | 153° C. |

(4) Further, FIG. 1 shows infrared absorption spectra (KBr method) of octyl gluconamide, decyl gluconamide, dodecyl gluconamide, and tetradecyl gluconamide. From FIG. 1, characteristic were the absorption around 3,310 cm$^{-1}$ (a in the figure) attributed to an alcohol of gluconic acid, the absorption around 2,917 cm$^{-1}$ (b in the figure) and 2,849 cm$^{-1}$ (c in the figure) each attributed to an alkyl group, and the absorption around 1,624 cm$^{-1}$ (d in the figure) attributed to a carbonyl group (amide).

Example 2

The alkyl amide derivative, which was obtained by subjecting, to ring-opening polymerization, an alkylamine having an amino group at one end of a linear alkane and having 4 to 16 carbon atoms, and gluconolactone, was examined for its relationship among the number of carbons in the alkyl group, the temperature at the time of the reaction with a boron aqueous solution, and the amount of boron removed. At each of temperatures of 4° C. (•), 25° C. (□), and 65° C. (♦), the relationship between the number of carbons in the alkyl group and the amount of boron removed was as shown in FIG. 2. As clear from FIG. 2, when the alkyl group had 4 carbon atoms, the amount of boron removed was 0 or extremely small regardless of the temperature, and when the alkyl group had 6 carbon atoms, the amount of boron removed was about 0.5 mmol/g regardless of the temperature. Further, when the alkyl group had 7 to 8 carbon atoms, the amount of boron removed as high as 2.0 to 2.5 mmol/g was exhibited regardless of the temperature. On the other hand, when the temperature was low (4° C.), in an amide derivative having 10 to 16 carbon atoms, as the number of carbons became larger, the amount of boron removed was lowered. Further, when the temperature was higher (25° C.) than that in the above-mentioned case, in an amide derivative having 12 to 16 carbon atoms, as the number of carbons became larger, the amount of boron removed was lowered. However, when the temperature was high (65° C.), in the amide derivative having 12 to 16 carbon atoms, the amount of boron removed as high as 2.0 mmol/g or more was exhibited regardless of the number of carbons.

This is probably due to the following reasons: when the alkyl group has a short length, even if the amide derivative binds to boron, the alkyl group cannot exert a sufficient hydrophobicity, and hence, the complex of the amide derivative and boron has a high solubility in water regardless of the reaction temperature, and the flocculation is not formed; while when the alkyl group has a long length, if the temperature is low, the amide derivative exhibits a strong hydrophobicity, and hence is not sufficiently dispersed in boron-containing water, and the amount of the amide derivative that contributes to the boron adsorption decreases, with the result that an apparent amount of boron removed may be lowered. In view of those results, the amide derivative contained in the boron adsorbent of the present invention has an alkyl group having 7 to 16 and preferably 7 to 13 carbon atoms.

Example 3

Octyl gluconamide and dodecyl gluconamide, each of which was one of the alkyl amide derivatives, were determined for their adsorption isotherms. FIG. 3 shows the results. As clear from FIG. 3, the amount of boron removed by octyl gluconamide (□) at 100 ppm as an equilibrium concentration of boron was 2.9 mmol/g, and the amount of boron removed at 10 ppm as the effluent standard was 1.8 mmol/g. The amount of boron removed became 0.5 mmol/g or less when the equilibrium concentration of boron was 1 ppm or less. Further, the amount of boron removed by dodecyl gluconamide (♦) at 100 ppm as an equilibrium concentration of boron was 2.3 mmol/g, and the amount of boron removed at 10 ppm as the effluent standard was 1.3 mmol/g. The amount of boron removed was 0.5 mmol/g or less when the equilibrium concentration of boron was 2 ppm or less. This reveals that both of the amide derivatives have an extremely high boron removing ability.

Example 4

Dodecyl gluconamide and sodium dodecyl sulfate were mixed in a predetermined amount, supplemented with 30 mL of water, and dissolved with heating. After being cooled to room temperature, the solution was further supplemented with 50 mL of water and 10 mL of a 1,000 ppm boric acid aqueous solution, and adjusted so as to have a pH of 9.3 with a sodium hydroxide aqueous solution. Then, a sample was prepared by adding 1 mL of a 1 mol/L calcium chloride aqueous solution, adding water so that the total volume might be 100 mL, and stirring. Further, for the purpose of comparison, the following samples were each prepared: a sample obtained by: suspending predetermined amounts of aluminum sulfate tetradeca- to octadecahydrate and calcium hydroxide in 80 mL of water; then adding 10 mL of a 1,000 ppm boric acid aqueous solution thereto; adjusting the pH to 9.1 with a sodium hydroxide aqueous solution; and further adding water so that the total volume might be 100 mL, and stirring; and a sample obtained by: adding a predetermined amount of Chelest Fiber (GCP) to 90 mL of water; adding 10 mL of a 1,000 ppm boric acid aqueous solution thereto; adjusting the pH to 9.1 with a sodium hydroxide aqueous solution; and further adding water so that the total volume might be 100 mL, and stirring. The respective samples were reacted at room temperature for 1 hour and then centrifuged to remove a flocculate or a fiber. Then, measurement was performed for the concentration of boron in the supernatant. In the respective samples, FIG. 4 shows the relationship between the concentration of the main body of the boron adsorbent other than an additive, that is, the concentration of dodecyl gluconamide or aluminum sulfate tetradeca—to octadecahydrate or Chelest Fiber, and the concentration of boron in the solution. As clear from FIG. 4, the amount of boron removed was the largest in the case of using dodecyl gluconamide (•). The amounts of boron removed was large in the case of using Chelest Fiber GCP (◆) and the aluminum sulfate method (□) in the stated order. In particular, it was found that dodecyl gluconamide had an excellent ability to reduce the concentration of boron in a boron solution to a low concentration in a small agent addition amount.

Example 5

300 mg of octyl gluconamide (OG), which was one of the alkyl amide derivatives, were dissolved in 8 mL of water, the pH of which had been adjusted to 12.2. Added to the resultant was 1 mL of a 1,000 ppm boric acid aqueous solution, followed by a reaction with stirring at room temperature for 30 minutes. Thus, a solution A was obtained. On the other hand, 300 mg of sodium dodecyl sulfate (SDS) were dissolved in 8 mL of water, the pH of which had been adjusted to 12.2. Added to the resultant was 1 mL of a 1,000 ppm boric acid aqueous solution, followed by a reaction with stirring at room temperature for 30 minutes. Thus, a solution B was obtained. Predetermined amounts according to Table 3 of the solution A and the solution B were each loaded into a square cell equipped with a magnetic stirrer bar, and stirred, and the light transmittance at 450 nm was time-dependently measured. At the time of 30 seconds after the start of the measurement, 0.1 mL of a 1 mol/L calcium chloride aqueous solution was injected into the square cell for the purpose of causing the flocculation. FIGS. 5 show time-dependent change in the flocculation by the addition of calcium chloride in a cell loaded with 1.4 mL of the solution A only (upper left part in figures), a cell loaded with 1.4 mL of the solution B only (upper right part in figures), and a cell loaded with a solution obtained by mixing 0.7 mL of the solution A and 0.7 mL of the solution B (lower left part in figures). Further, the solution in the cell after the reaction was recovered and centrifuged to remove the flocculation. The obtained supernatant was measured for the concentration of boron. The amount of boron removed per octyl gluconamide contained in the cell was measured. Table 3 shows the amount of boron removed, and the light transmittance of the sample immediately after the addition of calcium and 5 minutes after the addition of calcium collectively.

TABLE 3

| Solution A (mL) | Solution B (mL) | Light transmittance (%) Immediately after addition | Light transmittance (%) 5 minutes after addition | Amount of boron removed (mmol/g) |
|---|---|---|---|---|
| 0.00 | 1.40 | 0.4 | 0.7 | 0.0 |
| 0.35 | 1.05 | 0.7 | 0.9 | 2.0 |
| 0.70 | 0.70 | 0.7 | 69.2 | 2.2 |
| 1.05 | 0.35 | 0.7 | 42.6 | 2.1 |
| 1.40 | 0.00 | 1.1 | 0.9 | 2.2 |

As clear from Table 3, when sodium dodecyl sulfate only was loaded, no boron could be removed. On the other hand, when octyl gluconamide and sodium dodecyl sulfate were loaded, and when octyl gluconamide only was loaded, the amount of boron removed was 2.0 mmol/g or more in both cases.

On the other hand, when the mass ratio of octyl gluconamide to sodium dodecyl sulfate was 1:1 or 1.05:0.35, the light transmittance 5 minutes after the addition was higher than that immediately after the addition. In other words, it is conceivable that the flocculation, which had been small immediately after the addition, became larger 5 minutes after the addition.

Example 6

Octyl gluconamide (OG) and sodium dodecyl sulfate (SDS) were blended at a weight ratio of 1:1 and mixed by sufficient trituration in a mortar. To 100 mL of wastewater from tilery, the pH of which had been adjusted to 12.2 by adding a small amount of a 10 mol/L sodium hydroxide aqueous solution, each predetermined amount according to Table 4 of the above-mentioned mixed powder of octyl gluconamide and sodium dodecyl sulfate was added, and was dissolved by stirring at room temperature (18° C.) for 30 minutes. To the respective samples, a 5 mol/L calcium chloride aqueous solution was added in a predetermined amount according to Table 4, and the whole was stirred, followed by a reaction at room temperature (18° C.) for 30 minutes for the purpose of causing the flocculation. 10 mL each of the samples after the reaction were taken, and the respective samples were centrifuged to remove the flocculation. Then, the recovered supernatant was measured for the concentration of boron. Table 4 shows the results. Further, FIG. 6 shows the relationship between the concentration of octyl gluconamide and the concentration of boron.

TABLE 4

| Amount of OG-SDS mixed powder added (g) | Concentration of OG in wastewater (% by mass) | Amount of 5 mol/L calcium chloride aqueous solution added (mL) | Concentration of boron (ppm) |
|---|---|---|---|
| 0.0 | 0.0 | 0.0 | 402.5 |
| 0.8 | 0.4 | 0.4 | 276.1 |
| 2.0 | 1.0 | 1.0 | 71.5 |
| 4.0 | 2.0 | 2.0 | 9.1 |
| 8.0 | 4.0 | 4.0 | 0.2 |

As clear from Table 4 and FIG. 6, the initial concentration of boron in boron-containing wastewater was about 400 ppm, and the concentration of boron was reduced depending on the amount of the above-mentioned mixed powder of octyl gluconamide and sodium dodecyl sulfate added. When boron-containing wastewater contained octyl gluconamide in a concentration of 2% by mass or more, the concentration of boron in wastewater was below 10 ppm as the effluent standard value.

Example 7

300 mg of octyl gluconamide (OG) were dissolved in 8 mL of water, the pH of which had been adjusted to 12.2. To the resultant was added 1 mL of a 1,000 ppm boric acid aqueous solution and the reaction was performed while stirring at room temperature for 30 minutes. Thus, a solution A was obtained. On the other hand, 300 mg of each of various anionic surfactants according to Table 5 were dissolved in 8 mL of water, the pH of which had been adjusted to 12.2. To the resultant added was 1 mL of a 1,000 ppm boric acid aqueous solution and the reaction was performed while stirring at room temperature for 30 minutes. Thus, a solution B was obtained. 0.7 mL of the solution A and 0.7 mL of the solution B were loaded into a square cell equipped with a magnetic stirrer bar and stirred, and the light transmittance at 450 nm was time-dependently measured. At the time of 30 seconds after the start of the measurement, 0.1 mL of a 1 mol/L calcium chloride aqueous solution was injected into the square cell to cause flocculation. The solution in the cell after the reaction was recovered and centrifuged to remove the flocculation. The concentration of boron in the supernatant was measured. Then, measurement was performed for the amount of boron removed per octyl gluconamide contained in the cell. Table 5 shows the amount of boron removed, and the light transmittance of the sample immediately after the addition of calcium and 5 minutes after the addition of calcium collectively.

TABLE 5

| Anionic surfactant | Light transmittance (%) Immediately after addition | Light transmittance (%) 5 minutes after addition | Amount of boron removed (mmol/g) |
|---|---|---|---|
| Surfactant-free (1.4 mL of solution A only) | 2.7 | 1.1 | 2.0 |
| Sodium dodecyl sulfate | 0.8 | 61.4 | 2.2 |
| Sodium N-Dodecanoyl-N-methyl glycinate | 0.5 | 48.1 | 1.8 |
| Sodium alkyl benzene sulfonate | 0.6 | 62.2 | 2.2 |

As described in Example 5, even in the case where octyl gluconamide only was loaded (the case where the solution A only was loaded), the flocculation was achieved, there was a boron removing ability, but a flocculating ability was not enhanced. On the other hand, even in the case where any anionic surfactant of sodium dodecyl sulfate, sodium N-dodecanoyl-N-methyl glycinate, and sodium alkyl benzene sulfonate was used, there was a remarkable difference in the light transmittance immediately after the addition of calcium chloride and 5 minutes after the addition of calcium chloride, compared with the case where octyl gluconamide was used alone. Further, those anionic surfactants did almost no change in a boron removing ability of the amide derivative.

Example 8

300 mg of octyl gluconamide and 300 mg of sodium dodecyl sulfate were dissolved in 87 mL of water, the pH of which had been adjusted to 12.2. To the resultant were added 10 mL of a 1,000 ppm boric acid aqueous solution. The resultant was stirred at room temperature for 30 minutes. Subsequently, 3 mL of a solution (1 mol/L) of the cation source having two or more valencies according to Table 6 were added thereto, and the whole was further stirred for 30 minutes to cause the flocculation. 10 mL each of the respective samples were taken and centrifuged to remove the flocculation. The supernatant was measured for the concentration of boron by an azomethine method. Table 6 shows the results.

TABLE 6

| Cation source having two or more valencies and salt thereof added | Amount of boron removed mmol/g |
|---|---|
| Calcium chloride | 2.5 |
| Calcium hydroxide (used as suspension) | 1.9 |
| Calcium carbonate (used as suspension) | 0.3 |
| Magnesium chloride | 0.3 |
| Magnesium sulfate | 0.3 |
| Iron chloride | 0.4 |
| Aluminum chloride | 0.5 |
| Copper sulfate | 0.4 |
| Zinc sulfate | 2.4 |
| Lead nitrate | 1.9 |
| Manganese chloride | 2.3 |
| Polydimethyl diallyl ammonium chloride | 1.4 |
| Polyethyleneimine (EPOMIN SP-012) | 0.3 |

In the investigated cation sources and salts thereof, calcium chloride, calcium hydroxide, zinc sulfate, lead nitrate, manganese chloride, and polydimethyl diallyl ammonium chloride each caused sufficient flocculation, thereby providing a large amount of boron removed. Even calcium hydroxide (slaked lime) with a poor solubility had a good boron removing ability. Further, zinc and lead cannot be used in an actual treatment of boron-containing wastewater. However, suggestion is made that in the case where boron-containing water contains those deleterious heavy metals, when the complex of boron and the amide derivative flocculates by the cation having two or more valencies by adding the boron adsorbent of the present invention, those heavy metals are simultaneously removed by being uptaken into the flocculate. On the other hand, the use of a magnesium salt resulted in a relatively low amount of boron removed. The use of iron, aluminum, or copper also resulted in a relatively low amount of boron removed, probably because metal ions themselves may flocculate and precipitate at a higher pH in those metals.

Example 9

By using octylamine or dodecylamine, and glucoheptonolactone as raw materials, an alkyl amide derivative was obtained. That is, 12.9 g (0.1 mol) of octylamine or 18.5 g (0.1 mol) of dodecylamine were added into 200 mL of methanol, respectively, and stirred and dissolved in a hot water bath (50° C.). To each of the resultant added were 20.8 g (0.1 mol) of glucoheptonolactone powder and the reaction was performed. In this case, glucoheptonolactone rapidly reacted with each amine, and as the reaction proceeded, the powder disappeared and a white condensate was observed in each case.

After that, the reaction solution was cooled by being left to stand in ice water for the purpose of sufficiently precipitating a crystal of the condensate. Then, the crystal was recovered. The recovered crystal was dissolved in hot water at 90° C. and then cooled again by being left to stand in ice water for the purpose of achieving sufficient recrystallization. After that, the crystal was recovered, further dissolved in methanol heated to 60° C., and then cooled again by being left to stand in ice water for the purpose of achieving sufficient recrystallization of the condensate. Thus, the precipitated crystal was recovered. After the recrystallization operation was performed twice in total, 26.8 g of octyl glucoheptonamide and 36.3 g of dodecyl glucoheptonamide were obtained by drying at 60° C. overnight.

1) Octyl Glucoheptonamide
Melting point: 152° C.
IR (KBr): 3333, 2918, 2851, 1645, 1549, 1452, 1076, 1047, 613 cm$^{-1}$ (FIG. 7)

2) Dodecyl Glucoheptonamide
Melting point: 153° C.
IR (KBr): 3342, 2918, 2851, 1645, 1549, 1452, 1366, 1086, 1047, 864, 613 cm$^{-1}$ (FIG. 7)

Subsequently, the resulting alkyl amide derivatives were examined for their amount of boron removed at reaction temperatures of 4° C., 22° C., and 60° C. Table 7 shows the results.

TABLE 7

| Amide derivative (carbon length) | Amount of boron removed (mmol/g) | | |
|---|---|---|---|
| | 4° C. | 22° C. | 60° C. |
| Octyl glucoheptonamide (C8) | 2.6 | 2.7 | 2.6 |
| Dodecyl glucoheptonamide (C12) | 1.1 | 1.6 | 2.4 |

Octyl glucoheptonamide exhibited a large amount of boron removed both at a lower temperature and at a higher temperature. On the other hand, dodecyl glucoheptonamide exhibited a larger amount of boron removed at a higher temperature.

Example 10

By using octamethylenediamine or dodecamethylenediamine, and gluconolactone as raw materials, an alkylene diamide derivative was obtained. That is, 14.4 g (0.1 mol) of octamethylenediamine or 20.0 g (0.1 mol) of dodecamethylenediamine were added into 200 mL of methanol, respectively, and stirred and dissolved in a hot water bath (50° C.). Added to each of the resultant were 35.6 g (0.2 mol) of gluconolactone powder, followed by a reaction with stirring. In this case, gluconolactone powder rapidly reacted with each diamine, and as the reaction proceeded, the powder disappeared. In each case, a white condensate was observed.

After that, the reaction solution was cooled by being left to stand in ice water for the purpose of sufficiently precipitating a crystal of the condensate. Then, the crystal was recovered. The recovered crystal was dissolved in hot water at 90° C. and then cooled again by being left to stand in ice water or at room temperature for the purpose of achieving sufficient recrystallization. The crystal was recovered, further dissolved in methanol heated to 60° C., and then cooled again by being left to stand in ice water for the purpose of achieving sufficient recrystallization. Thus, the precipitated crystal was recovered. After the recrystallization operation was performed twice in total, 34.1 g of octamethylene digluconamide and 46.3 g of dodecamethylene digluconamide were obtained by drying at 60° C. overnight.

1) Octamethylene Digluconamide
Melting point: 194° C.
IR (KBr): 3313, 2918, 2851, 1626, 1549, 1443, 1134, 1086, 1028 cm$^{-1}$ (FIG. 8)

2) Dodecamethylene Digluconamide
Melting point: 201° C.
IR (KBr): 3313, 2918, 2851, 1626, 1549, 1472, 1443, 1134, 1086, 1028 cm$^{-1}$ (FIG. 8)

Subsequently, the resulting alkylene diamide derivatives were examined for the amount of boron removed at each of reaction temperatures of 4° C., 22° C., and 60° C. Table 8 shows the results.

TABLE 8

| Diamide derivative (carbon length) | Amount of boron removed (mmol/g) | | |
|---|---|---|---|
| | 4° C. | 22° C. | 60° C. |
| Octamethylene digluconamide (C8) | 0.1 | 0.2 | 0.8 |
| Dodecamethylene digluconamide (C12) | 2.4 | 2.6 | 2.7 |

The larger the number of carbons in the alkylene group was, the larger the amount of boron removed was. Compared with the above-mentioned alkyl gluconamide, the number of carbons of a hydrocarbon group optimal for removing boron was shifted toward longer chain length. Further, the dependency of the amount of boron removed on temperature observed in the alkyl gluconamide (see FIG. 2) was not observed in the alkylene (C8 to 12) digluconamide. This is probably because the diamide derivative has two hydrophilic groups derived from gluconic acid, and thus, does not exhibit a higher insolublity in water unless the number of carbons in the hydrocarbon groups is further increased.

Example 11

Octamethylenediamine, nonamethylenediamine, decamethylenediamine, or dodecamethylenediamine, and glucoheptonolactone were used as raw materials to afford an alkylene diamide derivative. That is, 14.4 g (0.1 mol) of octamethylenediamine, 15.8 g (0.1 mol) of nonamethylenediamine, 17.2 g (0.1 mol) of decamethylenediamine, or 20.0 g (0.1 mol) of dodecamethylenediamine were added into 200 mL of methanol, and the whole was stirred and dissolved in a hot water bath (50° C.). Added to each of the resultant were 41.6 g (0.2 mol) of glucoheptonolactone powder to perform a reaction. In this case, glucoheptonolactone powder rapidly reacted with each diamine, and as the reaction proceeded, the powder disappeared and a white condensate was observed in each case.

After that, the reaction solution was cooled by being left to stand in ice water for the purpose of sufficiently precipitating a crystal of the condensate. Then, the crystal was recovered. The recovered crystal was dissolved in hot water at 90° C. and then cooled again by being left to standing in ice water for the purpose of achieving sufficient recrystallization. The crystal was recovered, further dissolved in methanol heated to 60° C., and then cooled again by being left to stand in ice water for the purpose of achieving sufficient recrystallization. Thus, the precipitated crystal was recovered. After the recrystallization operation was performed twice in total, 34.9 g of octamethylene diglucoheptonamide, 43.4 g of nonamethylene diglucoheptonamide, 52.7 g of decamethylene diglucoheptonamide, and 57.6 g of dodecamethylene diglucoheptonamide were obtained by drying at 60° C. overnight.

1) Octamethylene Diglucoheptonamide
Melting point: 191° C.
IR (KBr): 3333, 2928, 2851, 1645, 1549, 1452, 1076, 1047, 613 cm$^{-1}$ (FIG. 9)

2) Dodecamethylene Diglucoheptonamide

Melting point: 174° C.
IR (KBr): 3332, 2918, 2851, 1645, 1539, 1472, 1076, 1047 cm$^{-1}$ (FIG. 9)

Subsequently, the resulting alkylene diamide derivatives were examined for the amount of boron removed at each of reaction temperatures of 4° C., 22° C., and 60° C. Table 9 shows the results.

TABLE 9

| Diamide derivative (carbon length) | Amount of boron removed (mmol/g) | | |
|---|---|---|---|
| | 4° C. | 22° C. | 60° C. |
| Octamethylene diglucoheptonamide (C8) | 0.8 | 1.1 | 2.1 |
| Nonamethylene diglucoheptonamide (C9) | 1.6 | 2.0 | 2.6 |
| Decamethylene diglucoheptonamide (C10) | 1.7 | 2.3 | 2.7 |
| Dodecamethylene diglucoheptonamide (C12) | 1.9 | 2.3 | 2.5 |

The larger the number of carbons contained in the alkylene group was, the larger the amount of boron removed was. The amount of boron removed by the diamide derivative does not remarkably depend on temperature. However, on average, there was a tendency that the higher temperature resulted in the larger amount of boron removed.

Industrial Applicability

The amide derivative as an essential component of the boron adsorbent of the present invention adsorbs a large amount of boron per unit weight. Therefore, the boron adsorbent of the present invention efficiently adsorbs boron in the solution, and can be widely used ranging from a high concentration of boron-containing water to a low concentration of boron-containing water. Then, the addition of the cation source having two or more valencies causes the flocculation of the amide derivative that adsorbed boron, which may be efficiently separated from water. Further, when the boron adsorbent containing the amide derivative and the anionic surfactant is used for boron-containing water, the flocculation caused by the addition of the cation source having two or more valencies becomes bigger and stronger, which allows the removal of boron at a higher rate. Still further, when the kit for removing boron of the present invention, which includes a combination of the boron adsorbent and the cation source having two or more valencies, is used to treat boron-containing water, excellent adsorption and flocculation rates of boron may be achieved simply. Yet still further, a waste volume may also be greatly reduced because the formed flocculate may be separated from water and then incinerated.

What is claimed is:

1. A method of removing boron, comprising:
under an alkaline condition,
adding a boron adsorbent to boron-containing water; and
further adding a cation source having two or more valencies,
wherein the boron adsorbent comprises an amide derivative represented by the following general formula (1):

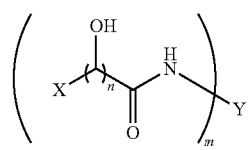

wherein m represents 1 or 2; X each independently represents —CH$_2$OH, —CHO, or —COOH; n each independently represents an integer of 2 to 5; and Y represents a monovalent hydrocarbon group having 6 to 16 carbon atoms when m represents 1, and represents a divalent hydrocarbon group having 8 to 18 carbon atoms when m represents 2.

2. A method of removing boron according to claim 1, wherein X represents —CH$_2$OH in the general formula (1).

3. A method of removing boron according to claim 1, wherein n represents 4 or 5 in the general formula (1).

4. A method of removing boron according to claim 1, wherein the boron adsorbent further comprises an anionic surfactant.

5. A method of removing boron according to claim 4, wherein the anionic surfactant is a sulfonate surfactant or a sulfate surfactant.

6. A method of removing boron according to claim 4, wherein the anionic surfactant is at least one kind selected from the group consisting of a higher alkyl sulfate, an alkyl ether sulfate, an N-acyl glycinate, a higher fatty acid amide sulfonate, a sulfosuccinate, an alkyl benzene sulfonate, an N-acyl glutamate, a higher fatty acid ester sulfate, a sulfated oil, an α-olefin sulfonate, a higher fatty acid ester sulfonate, a secondary alcohol sulfate, a higher fatty acid alkylolamide sulfate, an alkanoyl monoethanolamide succinate, and a ditriethanolamine N-alkanoyl aspartate.

* * * * *

UNITED STATES PATENT AND TRADEMARK OFFICE
CERTIFICATE OF CORRECTION

| | | |
|---|---|---|
| PATENT NO. | : 8,236,180 B2 | Page 1 of 1 |
| APPLICATION NO. | : 12/600215 | |
| DATED | : August 7, 2012 | |
| INVENTOR(S) | : Yabusaki | |

It is certified that error appears in the above-identified patent and that said Letters Patent is hereby corrected as shown below:

Item (56) References Cited on Page 2, in column 2 at line 18, Under Other Publications, change "Prograss" to --Progress--.

IN THE SPECIFICATIONS:

In column 6 at line 6, Change "tetradecarnethylenediamine," to --tetradecamethylenediamine,--.

In column 9 at line 9, Change "flouride," to --fluoride,--.

In column 12 at line 36, Change "Table" to --Table 1--.

In column 13 at line 64, Change "recrystallizion" to --recrystallization--.

In column 17 at line 22, Change "tetradeca—to" to --tetradeca- to--.

In column 22 at line 29, Change "insolublity" to --insolubility--.

Signed and Sealed this
Nineteenth Day of March, 2013

Teresa Stanek Rea
*Acting Director of the United States Patent and Trademark Office*